(12) United States Patent
Hong et al.

(10) Patent No.: US 8,715,716 B2
(45) Date of Patent: May 6, 2014

(54) METHODS FOR PRODUCING LOW CHOLESTEROL ANIMAL PRODUCTS USING HYPOCHOLESTEROLEMIC FEED SUPPLEMENTS AND PRODUCTS THEREFROM

(75) Inventors: Seong-Tshool Hong, Chonju (KR); Hyeon-Jin Kim, Chonju (KR); Dae-Kwon Lee, Chonju (KR); Won-Young Yang, Namwon (KR)

(73) Assignee: Jinis Biopharmaceuticals Co. (KR)

( * ) Notice: Subject to any disclaimer, the term of this patent is extended or adjusted under 35 U.S.C. 154(b) by 580 days.

(21) Appl. No.: 10/157,519

(22) Filed: May 29, 2002

(65) Prior Publication Data

US 2003/0194394 A1    Oct. 16, 2003

(51) Int. Cl.
| | | |
|---|---|---|
| *A23C 9/12* | (2006.01) | |
| *A23K 3/00* | (2006.01) | |
| *A23L 1/28* | (2006.01) | |
| *A01N 63/00* | (2006.01) | |
| *A01N 63/04* | (2006.01) | |
| *A01N 65/00* | (2009.01) | |
| *C12N 1/00* | (2006.01) | |
| *C12N 1/20* | (2006.01) | |
| *C12P 1/00* | (2006.01) | |
| *C12P 1/02* | (2006.01) | |
| *C12P 1/06* | (2006.01) | |

(52) U.S. Cl.
USPC ........ 424/442; 424/93.1; 424/93.3; 424/93.4; 424/93.5; 424/93.51; 426/53; 426/61; 435/41; 435/169; 435/171; 435/243; 435/252.4; 435/913; 435/932; 435/933; 435/945

(58) Field of Classification Search
USPC ........................................... 426/47; 424/93.1
See application file for complete search history.

(56) References Cited

U.S. PATENT DOCUMENTS

| | | | |
|---|---|---|---|
| 3,983,140 A | | 9/1976 | Endo et al. |
| 4,049,495 A | | 9/1977 | Endo et al. |
| 4,226,940 A | * | 10/1980 | Storrs .......................... 435/260 |
| 4,231,938 A | | 11/1980 | Monaghan et al. |
| 4,294,846 A | | 10/1981 | Albers-Schonberg et al. |
| 4,294,926 A | | 10/1981 | Monaghan et al. |
| 4,318,916 A | * | 3/1982 | Okamura et al. .......... 514/210.1 |
| 4,319,039 A | | 3/1982 | Albers-Schonberg |
| 4,323,648 A | | 4/1982 | Tanzawa et al. |
| 4,342,767 A | | 8/1982 | Albers-Schonberg et al. |
| 4,346,227 A | | 8/1982 | Terahara et al. |
| 4,351,844 A | | 9/1982 | Patchett et al. |
| 4,361,515 A | | 11/1982 | Terahara et al. |
| 4,376,863 A | | 3/1983 | Lam |
| 4,420,491 A | | 12/1983 | Albers-Schonberg et al. |
| 4,432,996 A | | 2/1984 | Gullo et al. |
| 4,444,784 A | | 4/1984 | Hoffman et al. |
| 4,450,171 A | | 5/1984 | Hoffman et al. |
| 4,739,073 A | | 4/1988 | Kathawala |
| 5,139,792 A | * | 8/1992 | Ware et al. ........................ 426/2 |
| 5,273,995 A | | 12/1993 | Roth |
| 5,340,594 A | * | 8/1994 | Barclay ........................... 426/49 |
| 5,362,638 A | | 11/1994 | Dahiya |
| 5,403,728 A | | 4/1995 | Jekkel et al. |
| 5,712,130 A | | 1/1998 | Hajko et al. |
| 5,908,622 A | * | 6/1999 | Barclay ....................... 424/93.1 |
| 6,046,022 A | | 4/2000 | Zhang et al. |
| 6,165,757 A | | 12/2000 | Ykema et al. |
| 6,177,121 B1 | | 1/2001 | Elkin et al. |
| 6,197,560 B1 | | 3/2001 | Seress et al. |
| 6,268,186 B1 | | 7/2001 | Sibeijn et al. |
| 6,271,001 B1 | * | 8/2001 | Clarke et al. ..................... 435/72 |
| 6,372,462 B2 | * | 4/2002 | Wasser et al. ................. 435/171 |
| 6,441,208 B2 | * | 8/2002 | Bijl et al. ........................... 554/8 |
| 6,506,402 B1 | * | 1/2003 | Winstrom ..................... 424/442 |
| 6,849,281 B2 | * | 2/2005 | Bodor et al. .................... 426/46 |

FOREIGN PATENT DOCUMENTS

| | | |
|---|---|---|
| CA | 2129416 | 2/1995 |
| DE | 30 06 216 A1 | 9/1980 |
| GB | 2046737 A | 2/1980 |
| GB | 2055100 A | 7/1980 |
| HU | 208 997 A | 2/1994 |

OTHER PUBLICATIONS

Derwent 1978836, JP 78027782 Abstract Only, see entire abstract, 1978.*
Alberts et al., "Mevinolin: A highly potent competitive inhibitor of hydroxymethylglutaryl-coenzymeA reductase and cholesterol-lowering agent", Proc. Natl. Acad. Sci. No. 7, pp. 3957-3961, Jul. 1980.
Endo et al., Monacolin K, a new hypo-cholesterolemic agent-produced by a *Monascus* species. The Journal of Antibiotics, Aug. 1979 pp. 852-854.
Hulcher et al. Inhibition of Hepatic Cholesterol Biosynthesis by 3,5-Dihydroxy-3,4,4-Trimethylvaleric Acid and its Site of Action, Archives of Biochemistry and Biophysic 146, 422-427 (1971).
Endo et al., "The Synthesis of Compactin and Monacolin K in Fungi", Journal of Antibiotics, Jun. 25, 1986 pp. 1609-1610.
Sutherland et al., "Recent advances in the biosynthetic studies of lovastatin", Current Opinion in Drug Discovery & Development 2001 vol. 4 No. 2, 229-236.
Heber et al., Cholesterol-lowering effects of a proprietary Chinese red-yeast-rice dietary supplement< Am. J. Clin Nutr. 1999; 69-231-6.

* cited by examiner

*Primary Examiner* — Debbie K Ware
(74) *Attorney, Agent, or Firm* — McDonnell Boehnen Hulbert & Berghoff LLP

(57) ABSTRACT

This invention provides methods and compositions for producing reduced cholesterol animal foodstuffs and products by feeding livestock and other food-producing animals with feed supplemented with microbial cultures containing hypocholesterolemic compounds produced by microorganisms comprising said microbial cultures. The invention provides low cholesterol poultry, eggs, meat, whole milk, and dairy products.

6 Claims, 6 Drawing Sheets

METHODS FOR PRODUCING LOW CHOLESTEROL ANIMAL PRODUCTS USING HYPOCHOLESTEROLEMIC FEED SUPPLEMENTS AND PRODUCTS THEREFROM

This application claims priority to Korean Patent Application No. 10-2002-0012103, filed Mar. 7, 2002, and to International Patent Application No. PCT/KR02/00516, filed Mar. 27, 2002.

BACKGROUND OF THE INVENTION

1. Field of the Invention

This invention generally relates to animal products for human consumption. The invention provides low cholesterol animal products for human consumption as food. Specifically, the invention provides methods for producing low cholesterol animal products by supplementing animal feed with microbial cultures containing hypocholesterolemic compounds and animal products produced using the methods. Methods for reducing serum cholesterol in humans and animals are also provided.

2. Background of the Related Art

Cholesterol is an essential constituent of cell membranes in humans and serves as a starting material for the synthesis of important biological compounds such as steroid hormones and bile acids. However, high serum cholesterol levels, termed hypercholesterolemia (more than 200 mg/dL of blood cholesterol), are a major risk factor for coronary artery disease, which leads inter alia to myocardial infarction. Coronary artery disease is the leading cause of human mortality in the United States and in many other developed countries, and is responsible for more deaths than all forms of cancer combined.

In the U.S., over half of the adult population has undesirably high serum cholesterol levels. For instance, 59 million American adults (32 percent) have blood cholesterol levels from 200 to 239 mg/dL (termed mild hypercholesterolemia), and about 38 million adults (21 percent) have serum cholesterol levels of 240 or above (termed severe hypercholesterolemia).

The amount of cholesterol obtained from diet for adult humans (especially from egg yolks, meat, poultry, fish, seafood and whole milk dairy products) is typically 350 mg daily, and another 800 mg are synthesized. It is generally accepted that high levels of cholesterol in the human diet can result in a rise in serum cholesterol and thereby increases the risk of cardiovascular diseases such as atherosclerosis, myocardial infarction, and hypertension. Therefore, medical practitioners recommend a reduced dietary intake of cholesterol (less than 300 mg/day) for all Americans (National Institutes of Health Consensus Development Panel).

Animal products, such as poultry, eggs, meat, and whole-milk dairy products, are recognized as excellent sources of dietary protein, minerals and other nutrients. However, health professionals recommend limited intake of these animal products due to their high content of cholesterol and fat. Cholesterol is present on average in amounts ranging from 70-150 mg per 100 g edible portion for beef (125 mg/100 g), calf (120), pork (90), turkey (80), duck (70), chicken (110), and shrimp (150). Chicken egg yolks have the highest cholesterol content of commonly-eaten foods (1330 mg/100 g).

As a result of the need to lower serum cholesterol in a general adult population with a diet high in cholesterol-rich foods, research and development efforts have been directed to low cholesterol foods, which the FDA defines as foods that are physiologically hypocholesterolemic (such as oatmeal, for example) that can provide both basic nutrition and may prevent coronary heart disease.

One area of research known in the art has been efforts to develop low cholesterol eggs, a highly nutritious but also high-cholesterol foodstuff. These efforts have been primarily directed at developing a low cholesterol, intact chicken egg, and include genetic selection, use of low fat and high fiber diets, and various egg selection methods. Of these, dietary measures are the most widely attempted methods, while the other methods are both technically difficult and time-consuming. However, there has been little success in the art in producing a low cholesterol egg regardless of the method employed.

An alternative to these methods for reducing the cholesterol content of domestic animal products is administration of pharmacological cholesterol-reducing agents known in the art to be useful in reducing serum cholesterol in humans. The most effective hypocholesterolemic agents for the treating hypercholesterolemia in current use for humans is the group of compounds, called statins, which inhibit cholesterol biosynthesis by inhibiting the key rate-limiting enzyme known as 3-hydroxy-3-methylglutaryl-coenzyme A reductase (HMG-CoA reductase). It is known that certain mevalonate derivatives inhibit the biosynthesis of cholesterol by inhibition of HMG-CoA reductase (Hulcher, 1971, *Arch. Biochem. Biophys.* 146: 422). The first such hypocholesterolemic compound discovered was compactin, also known as ML236B or mevastatin, which was isolated from cultures of Penicillium. Thereafter, a hypocholesterolemic compound found to be structurally related to compactin was isolated in fermentation products of several fungal species, including species from the *Monascus* and *Aspergillus* genera (Endo, 1979, *J. Antibiot.* 32: 852; Alberts et al., 1980, *Proc. Natl. Acad. Sci. USA* 77: 3957). The isolated active compounds (known as lovastatin, mevinolin, monacolin K, mevacor, MB530B, MK-803, or MSD803), their derivatives, methods of purification from several genera, and methods of semi-synthetic production from these derivatives have been reported in the art.

U.S. Pat. No. 3,983,140 discloses preparation of compactin (ML236B) from the genus *Penicillium*, preferably of the strain *P. citrinum* (strain ATCC 38065, ATCC 20606, SANK 18767).

U.S. Pat. No. 4,049,495 discloses preparation of compactin (ML236B) from the genus Penicillium, preferably of the strain *P. citrinum* (strain ATCC 38065, ATCC 20606, SANK 18767).

U.S. Pat. No. 4,231,938 discloses preparation of lovastatin (MSD803) from the genus Aspergillus, preferably *A. terreus* (ATCC 20541 and ATCC 20542) U.S. Pat. No. 4,294,846 discloses preparation of antihypercholesterolemic compounds from *Aspergillus* species.

U.S. Pat. No. 4,294,926 discloses preparation of lovastatin (MSD803) from *Aspergillus terreus*.

U.S. Pat. No. 4,319,039 discloses methods for isolating antihypercholesterolemic compounds from *Aspergillus terreus*.

U.S. Pat. No. 4,323,648 discloses preparation of lovastatin (monacolin K) from the genus *Monascus*, preferably *M. anka* (IFO 6540 or SANK 10171), *M. ruber* (ATCC 20657, SANK 10671, SANK 15177, SANK 18174, SANK 13778), *M. purpureus* (ATCC 16365, ATCC 16427, IFO 4513 or SANK 10271), *M. vitreus* (SANK 10960) and *M. paxii* (IFO 8201 or SANK 11172).

U.S. Pat. No. 4,342,767 discloses preparation of antihypercholesterolemic compounds from *Aspergillus* species.

U.S. Pat. No. 4,346,227 discloses derivatives of the antihypercholesterolemic compound ML236B.

U.S. Pat. No. 4,351,844 discloses preparation of lovastatin from the genus *Monascus*.

U.S. Pat. No. 4,361,515 discloses preparation of lovastatin from the genus *Monascus*.

U.S. Pat. No. 4,376,863 discloses preparation of lovastatin from the genus *Aspergillus*, preferably *A. terreus*.

U.S. Pat. No. 4,420,491 discloses preparation of antihypercholesterolemic compounds from *Aspergillus* species.

U.S. Pat. No. 4,432,996 discloses preparation of antihypercholesterolemic compounds from the genus *Penicillium*.

U.S. Pat. No. 4,444,784 discloses preparation of antihypercholesterolemic compound derivatives from *Aspergillus terreus*.

U.S. Pat. No. 4,450,171 discloses preparation of antihypercholesterolemic compound derivatives from *Aspergillus terreus*.

U.S. Pat. No. 4,739,073 discloses intermediates for synthesis of mevalonolactone antihypercholesterolemic compounds.

U.S. Pat. No. 5,362,638 discloses preparation of lovastatin from the genetically engineered strain of *A. oryzae* (ATCC 74135).

U.S. Pat. No. 5,403,728 discloses preparation of lovastatin from the genus Aspergillus, preferably *A. terreus* (ATCC 20541 and ATCC 20542) and *A. obscurus* (NCAIM(P)F 001189).

U.S. Pat. No. 5,712,130 discloses preparation of lovastatin from the genetically engineered strain of *A. oryzae* (ATCC 74135).

U.S. Pat. No. 6,046,022 discloses preparation of hypocholesterolemic compounds from the genus *Monascus*, employing red rice fermentation products.

U.S. Pat. No. 6,165,757 discloses preparation of lovastatin from the genus *Monascus*.

U.S. Pat. No. 6,197,560 discloses preparation of lovastatin from the genus *Monascus*.

U.S. Pat. No. 6,268,186 discloses preparation of lovastatin from the genus *Monascus*.

British Patent Specification No. GB 2,046,737 discloses preparation of antihypercholesterolemic compounds from *Monascus*.

British Patent Specification No. GB 2,049,664 discloses preparation of antihypercholesterolemic compounds from *Monascus*.

British Patent Specification No. GB 2,055,100 discloses preparation of antihypercholesterolemic compounds from *Monascus*.

German Patent No. DE 3,051,175 discloses preparation of antihypercholesterolemic compounds from *Monascus*.

German Patent No. DE 3,051,099 discloses preparation of antihypercholesterolemic compounds from *Monascus*.

German Patent No. DE 3,006,216 discloses preparation of antihypercholesterolemic compounds from *Monascus*.

German Patent No. 4,402,591 discloses preparation of lovastatin by microorganisms belonging to the *Pleurotus* genus, preferably *P. ostreatus, P. sapidus* and *P. saca*, Canadian Patent No. 2,129,416 discloses the preparation of lovastatin with a microorganism belonging to the Coniothyrium genus, preferably *Coniothyrium fuckelii* (ATCC 74227).

Hungarian Patent No. HU 208,997 discloses preparation of lovastatin from the genus Aspergillus, preferably *A. terreus* (ATCC 20541 and ATCC 20542) and *A. obscurus* (NCAIM (P)F 001189).

Other microorganisms capable of producing hypocholesterolemic compounds are known in the art, include species from the genera *Paecilomyces, Hypomyces, Doratomyces, Phoma, Eupenicillium, Gymnoascus,* and *Trichoderma* (Juzlova et al., 1996, *J. Indust. Micro.* 16: 163; Endo et al., 1986, *J. Antibiotics* 39: 1609; Sutherland et al., 2001, *Curr. Opin. Drug Discov. Devel.* 4: 229; U.S. Pat. No. 5,409,820; German Pat. No. 4,402,591). Statin-producing microorganisms or other hypocholesterolemic compound-producing microbial strains can be naturally occurring, genetically engineered, or altered from the wild type (such as mutant strain, for example *Paecilomyces* sp. M2016, *Phoma* sp. M4452, *Trichoderma longibrachiatum* M6735, and *Trichoderma pseudokoningii* M6828).

Using microorganisms capable of producing hypocholesterolemic compounds, several statins have been developed as HMG-CoA reductase inhibitors for the treatment of hypercholesterolemia. These include mevastatin (disclosed in U.S. Pat. No. 3,983,140), lovastatin or mevinolin (disclosed in U.S. Pat. No. 4,231,938), pravastatin (disclosed in U.S. Pat. No. 4,346,227), simvastatin (also referred to as synvinolin; disclosed in U.S. Pat. Nos. 4,444,784 and 4,450,171), fluvastatin (disclosed in U.S. Pat. No. 4,739,073), atorvastatin (disclosed in U.S. Pat. No. 5,273,995) and derivatives of these compounds. These compounds are highly active hypocholesterolemic agents and are available as prescription drugs: Atorvastatin (Lipitor; Pfizer), Fluvastatin (Lescol; Novartis), Lovastatin (Mevacor; Merck), Pravastatin (Pravachol; Bristol-Myers Squibb) and Simvastatin (Zocor; Merck).

In addition to prescription drugs, alternative sources of cholesterol-lowering dietary supplements include red yeast rice, which is the fermentation product of rice on red yeast, or cultures of lovastatin-producing *Monascus purpureus*. It is known that consumption of red yeast rice can reduce cholesterol concentration significantly in humans. Curiously, the quantities of lovastatin in red yeast rice are inadequate to explain the magnitude of the lowering of cholesterol observed when compared with lovastatin treatment (Herber et al., 1999, *Am. J. Clin. Nutr.* 69: 231-236). The cholesterol-lowering effect of red yeast rice is unlikely to result solely from the lovastatin contained in either red yeast or *Monascus*; it could result from a combination of additional, unidentified hypocholesterolemic compounds (if any) contained in the red yeast rice fermentation, but there have been no reports in the art concerning such putative additional hypocholesterolemic compounds.

Recently, significant reduction of the cholesterol content of egg yolk was demonstrated by oral administration of purified lovastatin to chickens (Elkin and Rogler, 1990, *J. Agric. Food Chem.* 38: 1635-1641, 1990; Elkin et al., 1993, *J. Agric. Food Chem.* 41: 1094-1101; U.S. Pat. Nos. 6,177,121 and 6,316, 041). Although the cholesterol-lowering effect was found to be satisfactory when the egg-laying chickens are fed high doses of lovastatin, use of these methods are impractical due to the high production cost of effective amounts of HMG-CoA reductase inhibitor and consequently high production cost of low cholesterol eggs.

Thus, inexpensive and effective methods for producing animal products having lower than naturally-occurring cholesterol levels, resulting in the production of low cholesterol foods are needed in the art. Furthermore, as illustrated with red yeast rice, methods for improving cholesterol lowering effect of animal feed on animal-derived foodstuffs by employing complete fermentation products rather than a single isolated species from the fermentation products are needed in the art.

SUMMARY OF THE INVENTION

The invention provides methods for producing animal products, particularly foodstuffs having lower than naturally-occurring levels of cholesterol. The invention also provides animal products, particularly foodstuffs having lower than naturally-occurring levels of cholesterol. The invention further provides animal feed comprising microbial cultures of microorganisms that produce antihypercholesterolemic (or hypocholesterolemic) compounds effective in lowering cholesterol levels in animals fed such animal feeds. Most preferably, the cholesterol-lowering compounds produced by the microbial cultures are fermentation products. The invention also provides such microbial cultures as animal feed supplements for producing low cholesterol meat, for producing low cholesterol milk and other dairy products when fed to milk-producing animals and for producing low cholesterol eggs when fed to egg-laying animals.

The invention provides methods for producing low cholesterol animal products comprising the step of feeding livestock with feed supplemented with microbial cultures comprising hypocholesterolemic compounds that are effective in reducing cholesterol concentration in animal meat, milk or eggs. In preferred embodiments, the microbial culture is a single or mixed cultures of microorganisms that naturally produces hypocholesterolemic compounds. In alternative preferred embodiments, the microbial culture is a genetically engineered or naturally-occurring mutant strain that produces hypocholesterolemic compounds, most preferably in greater amounts than the corresponding naturally-occurring, wild-type strain. Also provided by this aspect of the invention are meat, fish, milk, dairy products, or eggs produced by an animal fed animal feed supplemented with microbial cultures comprising hypocholesterolemic compounds that are effective in reducing cholesterol concentration in animal meat, milk or eggs.

The invention also provides animal feed comprising conventional animal feed appropriate for the animal species and foodstuff production from said animal, wherein the feed is supplemented with microbial cultures that produce antihypercholesterolemic compounds. In preferred embodiments, the hypocholesterolemic compounds are produced in the culture by fermentation. In additional preferred embodiments, the hypocholesterolemic compounds lower cholesterol concentration in foodstuffs obtained from animals fed with feed supplemented with the microbial culture by inhibiting cholesterol biosynthesis, by inhibiting re-absorption of bile acids along digestive tracts, or by facilitating conversion of cholesterols to bile acids.

Specific preferred embodiments of the present invention will become evident from the following more detailed description of certain preferred embodiments and the claims.

BRIEF DESCRIPTION OF THE DRAWINGS

FIG. 10 is a graph demonstrating the hypocholesterolemic effects in chicken eggs after administration of feed supplements comprising *Trichoderma longibrachiatum* fermentation products to egg-laying hens.

DETAILED DESCRIPTION OF PREFERRED EMBODIMENTS

Figure 1:
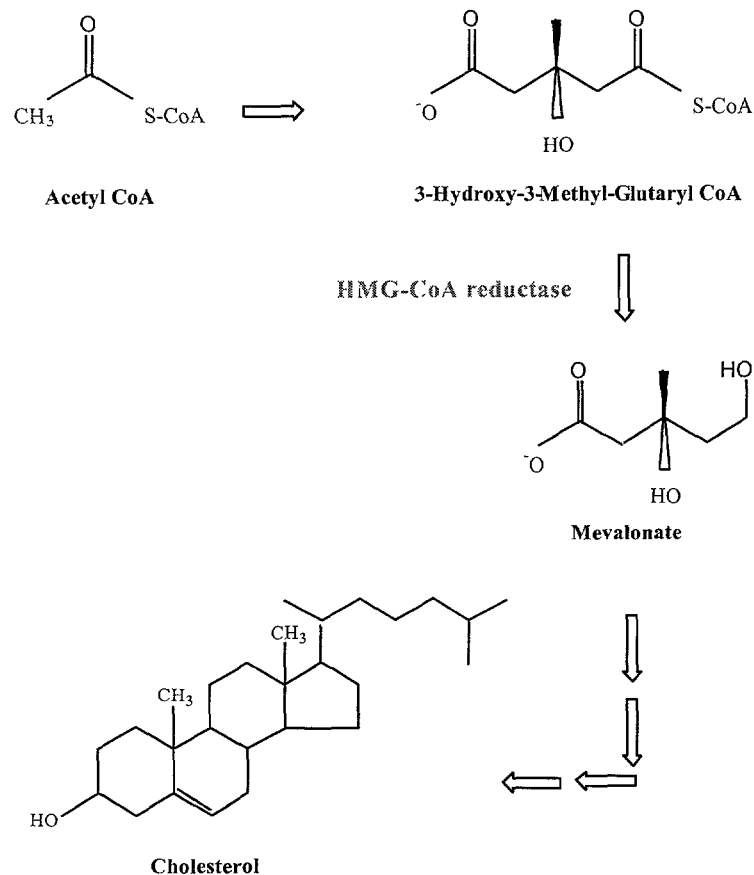
FIG. 1 depicts the cholesterol biosynthesis pathway and the key rate-limiting enzyme known as 3-hydroxy-3-methylglutaryl-coenzyme A reductase or HMG-CoA reductase.

This invention provides livestock and barnyard animal feed supplemented with microbial cultures that produce hypocholesterolemic compounds, and animal products with reduced levels of cholesterol for use as human foodstuffs.

As used herein, the following terms have the following meanings:

"Hypocholesterolemic feed supplement" is intended to encompass microbial culture in fermentation media containing hypocholesterolemic compounds effective in reducing blood cholesterol in an animal, most preferably livestock or barnyard animals used for food.

"Microbial culture" is intended to encompass single culture or mixed cultures of microorganisms capable of producing hypocholesterolemic compounds as fermentation products.

"Hypocholesterolemic compounds" is intended to encompass any compound effective in lowering cholesterol content of animals by least 10%. Preferred hypocholesterolemic compounds include but are not limited to lovastatin, mevinolin, monacolin K, mevacor, MB530B, MK803, or MSD 803 and derivatives thereof, and compactin and derivatives thereof.

"Animal," "livestock" and "barnyard animal" is intended to mean any domesticated animals raised for human consumption, including poultry such as chicken, duck, goose and turkey, and dairy animals such as cows and goats, and mammals such as cows, pigs, sheep, goats and lamb.

A "low cholesterol animal" is intended to mean any animal, particularly livestock or barnyard animals, having a blood cholesterol level that is reduced more than 10% compared to the animal raised in accordance with conventional animal husbandry methods.

"Low cholesterol animal products" is intended to encompass products, particularly edible products and most particularly foodstuffs, from animals, particularly livestock or barnyard animals, having a blood cholesterol level that is reduced more than 10% compared to the animal raised in accordance with conventional animal husbandry methods. Examples of low cholesterol animal products include low cholesterol milk, low cholesterol eggs, and low cholesterol meat.

This invention provides methods for producing low cholesterol animal products wherein animals are fed a feed supplemented with microbial cultures that produce hypocholesterolemic compounds. In preferred embodiments, the microbial cultures naturally produce said hypocholesterolemic compounds. In alternative preferred embodiments, the microbial cultures comprise genetically engineered microorganisms that produce the hypocholesterolemic compounds as a consequence of said genetic engineering. In preferred embodiments, the hypocholesterolemic compounds are produced by fermentation of the microbial culture. Said hypocholesterolemic compounds are effective in lowering animal blood cholesterol by inhibiting cholesterol biosynthesis, by inhibiting re-absorption of bile acids along digestive tracts, or by facilitating conversion of cholesterols to bile acids, or any combination of these features and properties. In preferred embodiments, the hypocholesterolemic compounds are HMG-CoA reductase inhibitors, including but not limited to monacolin K (or mevinolin), monacolin L, monacolin J, monacolin X, monacolin M, lovastatin, compactin and compounds derived therefrom. Biosynthesis of such HMG-CoA reductase inhibitors and their hypocholesterolemic activity is known in the art, as disclosed herein above (including, for example, in U.S. Pat. Nos. 3,983,140, 4,049,495, 4,137,322, 4,231,938, 4,294,846, 4,294,926, 4,319,039, 4,323,648, 4,342,767, 4,346,227, 4,351,844, 4,361,515, 4,376,863, 4,420,491, 4,432,996, 4,444,784, 4,450,171, 4,739,073, 5,273,995, 5,403,728, 5,712,130, 6,046,022, 6,165,757, 6,197,560, and 6,268,186). Hypocholesterolemic activity of unidentified compounds contained in addition to lovastatin in the fermentation product of *Monascus purpureusis* known in the art, as disclosed herein above (including in U.S. Pat. No. 6,046,022; Herber et al., 1999, *Am. J. Clin. Nutr.* 69: 231-236). In preferred embodiments, supplemented animal feed is fed to the animal at least once a day for at least two days, although longer regiments are contemplated by the invention. The extent and duration of feeding with the supplemented animal feed of this invention will depend on the age, weight, activity level and type, strain or species of animal, and to the composition of conventional animal feed fed to the animal.

The invention provides low cholesterol animals, low cholesterol animal products, and low cholesterol processed foods using the method described in this invention. Preferred embodiments include low cholesterol beef, lamb, pork, chicken, turkey, milk, cheese, yogurt, and eggs, as well as the animals from which these foods are derived or obtained.

Microbial cultures useful in the practice of the methods and animal feed supplements of the invention are any culture of a single type, strain or species of microorganism that produces one or a plurality of hypocholesterolemic compounds, or any mixed cultures thereof. The microorganism can be any microorganism that produces or is capable of producing the compound, including bacteria, yeast and fungi. Preferred microorganisms belong to genera including but not limited to *Aspergillus, Monascus, Penicillium, Paecilomyces, Hypomyces, Phoma, Pleurotus, Doratomyces, Eupenicillium, Gymnoascus, Trichoderma, Coniothyrium, Eubacterium,* and *Nocardia*.

The invention also provides hypocholesterolemic feed supplements comprising microbial cultures in fermentation media and containing hypocholesterolemic compounds in amounts effective for reducing blood cholesterol in an animal fed the supplemented animal feed. Most preferably, the food supplements of the invention comprise the microbial cultures and the fermentation media comprising multiple species of identified and unidentified hypocholesterolemic compounds. The invention provides animal feed compositions effective in reducing cholesterol in animal, wherein the feed comprises conventional animal feed appropriate for the animal to be fed supplemented with 0.1-30% (by weight) of a microbial culture that produces a cholesterol-reducing amount of one or a plurality of hypocholesterolemic compounds.

As provided by the invention, hypocholesterolemic compound-producing microorganisms are amplified in carbon-rich growth media and then incubated in an amino acid-rich fermentation media in order to facilitate production of hypocholesterolemic compounds as secondary metabolites. Plants and certain microorganisms are known to produce a variety of compounds, known as secondary metabolites through a secondary metabolite pathway. Secondary metabolites have a multiplicity of biological activities, including for example antibiotics, anticancer agents, and growth hormones. Growth in an amino acid-enriched media is known in the art to promoter production of secondary metabolites. Thus, in a preferred embodiment, production of hypocholesterolemic compounds in the microbial cultures of the invention is promoted by growth in an amino acid-enriched fermentation media. Preferably, fermentation media used in the practice of the methods of the invention contain cotton seed extracts as a nitrogen source, any powder or mixture of sugar, rice, corn, potato, and wheat as a carbon source, and sodium (Na), calcium (Ca), iron (Fe), copper (Cu), and manganese (Mn) as trace element components in order to promote the production of the secondary metabolites. More preferably, the fermentation media contains from about 0.5 to about 1.5% (by weight) cotton seed extract, from about 1.5 to about 4% carbon source, from about 0.1 to about 0.5% NaCl, from about 0.1 to about 0.5% $CaCO_3$, from about 0.01 to about 0.04% $FeCl_3.6H_2O$, from about 0.001 to about 0.002% $CuCl_2.2H_2O$, from about 0.001 to about 0.002% $MnCl_2.4H_2O$, from about 0.002 to about 0.006% $ZnCl_2$, from about 0.001 to about 0.002% $Na_2B_4O_7.10H_2O$, and from about 0.001 to about 0.002% $(NH_4)_6Mo_7O_{24}.4H_2O$ in water. An exemplary and non-limiting formulation of the fermentation media provided for use in the methods of the invention is set forth in Table 1. It will be recognized that conditions for secondary metabolite production are not limited to the specific fermentation media disclosed herein.

Specific protocols for preparing hypocholesterolemic feed supplements and low cholesterol animal products by administration of said hypocholesterolemic feed supplements to animals are as follows.

TABLE 1

Composition of the fermentation media

| Media | Composition (g/liter) |
|---|---|
| PST | 22.5 g sucrose, 10 g cotton seed extract, 3 g NaCl, 3 g $CaCO_3$, 40 mg $ZnCl_2$, 200 mg $FeCl_3 \cdot 6H_2O$, 10 mg $CuCl_2 \cdot 2H_2O$, 10 mg $MnCl_2 \cdot 4H_2O$, 10 mg $Na_2B_4O_7 \cdot 10H_2O$, 10 mg $(NH_4)_6Mo_7O_{24} \cdot 4H_2O$ |
| PRT | 22.5 g sucrose, 10 g rice, 3 g NaCl, 3 g $CaCO_3$, 40 mg $ZnCl_2$, 200 mg $FeCl_3 \cdot 6H_2O$, 10 mg $CuCl_2 \cdot 2H_2O$, 10 mg $MnCl_2 \cdot 4H_2O$, 10 mg $Na_2B_4O_7 \cdot 10H_2O$, 10 mg $(NH_4)_6Mo_7O_{24} \cdot 4H_2O$ |
| PCT | 22.5 g sucrose, 10 g corn, 3 g NaCl, 3 g $CaCO_3$, 40 mg $ZnCl_2$, 200 mg $FeCl_3 \cdot 6H_2O$, 10 mg $CuCl_2 \cdot 2H_2O$, 10 mg $MnCl_2 \cdot 4H_2O$, 10 mg $Na_2B_4O_7 \cdot 10H_2O$, 10 mg $(NH_4)_6Mo_7O_{24} \cdot 4H_2O$ |
| PPT | 22.5 g sucrose, 10 g potato, 3 g NaCl, 3 g $CaCO_3$, 40 mg $ZnCl_2$, 200 mg $FeCl_3 \cdot 6H_2O$, 10 mg $CuCl_2 \cdot 2H_2O$, 10 mg $MnCl_2 \cdot 4H_2O$, 10 mg $Na_2B_4O_7 \cdot 10H_2O$, 10 mg $(NH_4)_6Mo_7O_{24} \cdot 4H_2O$ |
| PWT | 22.5 g sucrose, 10 g wheat, 3 g NaCl, 3 g $CaCO_3$, 40 mg $ZnCl_2$, 200 mg $FeCl_3 \cdot 6H_2O$, 10 mg $CuCl_2 \cdot 2H_2O$, 10 mg $MnCl_2 \cdot 4H_2O$, 10 mg $Na_2B_4O_7 \cdot 10H_2O$, 10 mg $(NH_4)_6Mo_7O_{24} \cdot 4H_2O$ |

Protocol 1. Seed Culture

Microorganisms capable of expressing a secondary metabolite pathway are characterized by the fact that the rate of growth and division decrease significantly when secondary metabolite production is commenced. The purpose of seed culture is to promote growth and division of microorganisms and to repress the secondary metabolite pathway in liquid media that contains sufficient amounts of carbon sources and grown under aerobic conditions.

For preparing a seed culture, each microbial strain was incubated in an appropriate solid media for 5-8 days. Spores from fungi were collected and used for seed culture. Spores were inoculated in growth media that is carbon-rich to promote growth and cell division. More preferably, spores are inoculated in growth media in a baffled flask at a concentration of 0.2% (200 μL of spore suspension in 100 mL of growth media) and cultured for 2-4 days. For large scale assays, bioreactors can be used in two steps. For primary seed culture, $3.5 \times 10^9$ spores were inoculated into 1.5 L growth media in a 5 L aspirator bottle and cultured for 1-2 days in appropriate culture condition. For preparing secondary seed cultures, 150 mL of primary seed culture was inoculated into 60 L growth media in 150 L bioreactor and cultured for 1-2 days in appropriate culture condition.

Protocol 2. Production of Microbial Cultures Containing Hypocholesterolemic Compounds as Secondary Metabolites Once a seed culture is prepared according to Protocol 1, the microbial culture is incubated in fermentation media having a composition as shown in Table 1. The fermentation media described in Table 1 are relatively low in the amount of carbon-source nutrients and high in amino acid content, which growth conditions promote production and secretion of the secondary metabolites. The microbial culture is incubated under aerobic conditions, for example, by growth in 1 L baffled flask in 250 mL fermentation media and agitated at 150 rpm for 6-10 days. Larger scale growth conditions are achieved by inoculating 50 L (6% of total volume) of a secondary seed culture in 700 L fermentation media in a 1,000 L bioreactor and incubating the culture for 6-10 days with agitation at 80-120 rpm and maintenance of the culture pH between pH 5.8-6.3. Cultures prepared as described herein contain secondary metabolites as well as the fungus itself, and are used as feed supplements for animal in order to reduce serum cholesterol concentration and result in low-cholesterol animal products for human consumption as foodstuffs.

Protocol 3. Production of Low Cholesterol Animals by Administration of Hypocholesterolemic Feed Supplements Animals are fed a hypocholesterolemic food supplemented feed produced by mixing conventional animal feed appropriate for the animal to be fed with 0.1-30% (by weight) Of a microbial culture of the invention comprising a hypocholesterolemic compound and produced, for example, as described above in Protocol 2. A preferred feeding schedule is to feed the animal at least once a day with the supplemented feed for a period of more than two days duration.

The present invention may be better understood with reference to the accompanying examples that are intended for purposes of illustration only and should not be construed to limit the scope of the invention, as defined by the claims appended hereto.

EXAMPLE 1

Preparation of Microbial Cultures Containing Hypocholesterolemic Compounds

1. Seed Culture

Fungi were grown on an appropriate solid media shown in Table 2 by incubation for 5-8 days (Table 2). Spores from these fungi were collected and used to prepare a for seed culture. For the primary seed culture, $3.5 \times 10^8$ spore was inoculated into 150 mL growth media (YEME, comprising 0.3% yeast extract, 0.5% peptone, 0.3% malt extract, 34% sucrose, 1% glucose, and 0.1% $MgCl_2 \cdot 6H_2O$) in a 1 L baffled flask and cultured for 1-2 days under culture conditions appropriate for growth of the particular fungus. For producing the secondary seed culture, 150 mL of primary seed culture was inoculated into 60 L growth media in 150 L bioreactor and cultured for 1-2 days under appropriate culture condition.

TABLE 2

Solid media for collecting spore from fungi

| Species | Media components (g per 1 L) | Temp. |
|---|---|---|
| Aspergillus terreus ATCC 20542 | 20 g malt extract, 5 g peptone, 15 g agar | 26° C. |
| Paecilomyces sp. ATCC 20463 | 300 g diced potato, 20 g glucose, 15 g agar | 24° C. |
| Penicillium citrinum ATCC 20606 | 300 g diced potato, 20 g glucose, 15 g agar | 24° C. |
| Penicillium brevicompactum ATCC 9056 | 3 g $NaNO_3$, 1 g $K_2HPO_4$, 0.5 g $MgSO_4 \cdot 7H2O$, 0.5 g KCl, 0.01 g $FeSO_4 \cdot 7H2O$, 30 g sucrose, 15 g agar | 24° C. |
| Hypomyces chrysospermus IFO 7798 | 300 g diced potato, 20 g glucose, 15 g agar | 26° C. |
| Doratomyces nanus IFO 9551 | 300 g diced potato, 20 g glucose, 15 g agar | 26° C. |
| Phoma sp. ATCC 34505 | 300 g diced potato, 20 g glucose, 15 g agar | 24° C. |
| Eupenicillium sp. ATCC 52642 | 20 g malt extract, 20 g glucose, 1 g peptone, 20 g agar | 20° C. |
| Gymnoascus umbrinus IFO 8450 | 20 g potato, 20 g carrot, 15 g agar | 26° C. |

TABLE 2-continued

Solid media for collecting spore from fungi

| Species | Media components (g per 1 L) | Temp. |
|---|---|---|
| Trichoderma longibrachiatum ATCC 18648 | 25 g rabbit feed, 15 g agar | 26° C. |
| Trichoderma pseudokoningii ATCC 26801 | 30 g malt extract, 15 g agar | 24° C. |
| Pleurotus ostreatus ATCC 94 15 | 15 g glucose, 5 g peptone, 3 g malt extract, 3 g yeast extract, 20 g agar | 24° C. |
| Monascus purpureus IFO 4513 | 300 g diced potato, 20 g glucose, 15 g agar | 26° C. |
| Monascus ruber ATCC 20657 | 40 g glucose, 10 g peptone, 20 g agar | 26° C. |

2. Production of Microbial Culture Containing Hypocholesterolemic Compounds as Secondary Metabolites.

Once the seed culture is prepared, the microbial culture is incubated in fermentation media having a composition as shown in Table 1. Large scale fermentation cultures were prepared by inoculating 700 L fermentation media in a 1,000 L bioreactor with 50 L of the secondary seed culture and incubating the culture for 6-10 days under conditions appropriate for the microorganism comprising the culture and at 80-120 rpm and a pH maintained at pH 5.8-6.3. The produced microbial culture containing hypocholesterolemic compounds as secondary metabolites was added to commercial feed immediately or was stored at 4° C. until use.

EXAMPLE 2

Production of Low Cholesterol Eggs Using *Aspergillus terreus* Culture as Hypocholesterolemic Feed Supplements A culture of *A. terreus* (ATCC Accession No. 20542) was prepared as described in Example 1 above and added to commercial chicken feed at between 1-5% (by weight) and fed to egg-laying hens (33 weeks old) in every 12 hours for 3 weeks.

Figure 2:
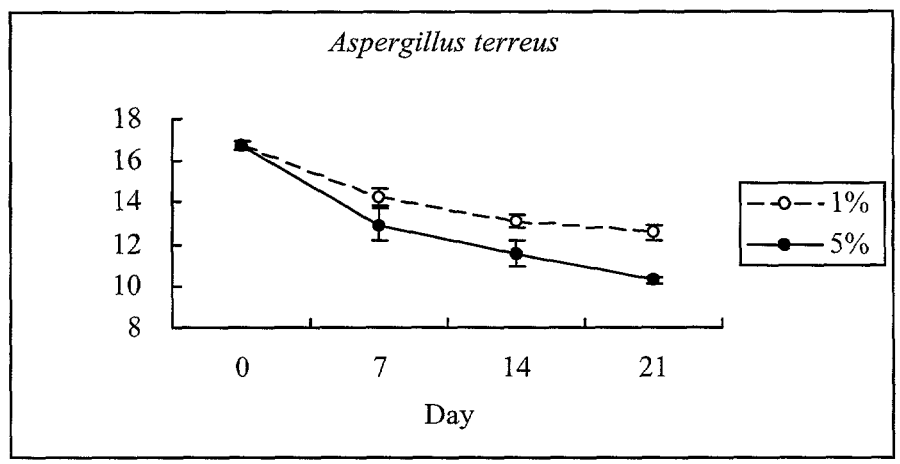
FIG. 2 is a graph demonstrating the hypocholesterolemic effects in chicken eggs after administration of feed supplements comprising *Aspergillus terreus* fermentation products to egg-laying hens.

The cholesterol content was analyzed from collected eggs using a chemical method employing o-phthalaldehyde as follows. Each egg was hard-boiled and the yolk was separated and crumbled. A mixture of chloroform/methanol (15 mL, 2:1 v/v) was added to 1 g of yolk and sonicated. After standing for 30 minutes, the homogeneous solution was filtered through a 0.45 μm membrane filter. Egg homogenate filtrates were analyzed for cholesterol content using o-phthalaldehyde by mixing thoroughly 0.1 mL of the filtrate, 0.3 mL of a solution of 33% (w/v) KOH in water, and 3 mL of 95% ethanol and then saponified for 15 min at 60° C. heat block. After saponification, 10 mL of n-hexane was added and mixed thoroughly. Two ml of freshly prepared o-phthalaldehyde solution (50 mg/dl in glacial acetic acid) was added to 1 mL of extracted cholesterol and incubated for 10 min. Absorbance was determined at 550 nm 30 min after the addition of 1 ml of concentrated sulfuric acid. The effect of cholesterol-lowering feed supplements is shown in Table 3 and FIG. 2.

TABLE 3

Cholesterol content of the eggs produced by administration of *A. terreus* culture as hypocholesterolemic feed supplements

| Feed supplement | Cholesterol content (mg)/yolk (g) | Cholesterol reduction (%) |
|---|---|---|
| 0% | 16.74 | 0 |
| 1% | 12.56 | 25 |
| 5% | 10.24 | 38 |

These results demonstrate that the supplemented animal feed of the invention is capable of reducing cholesterol content of egg yolks laid by hens feed the supplemented diet.

EXAMPLE 3

Figure 3:
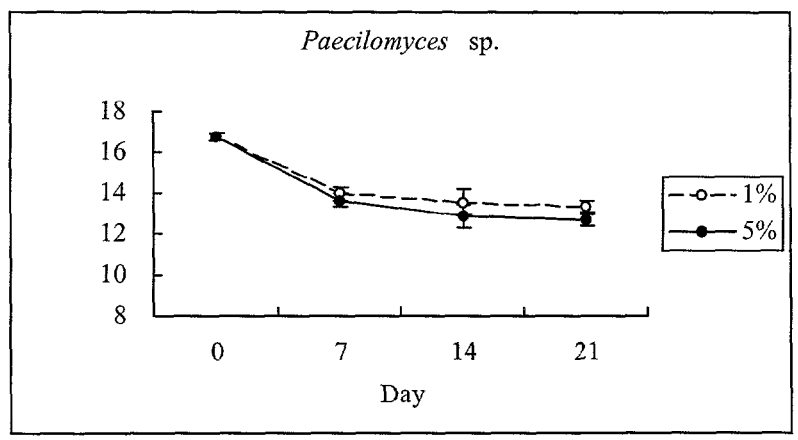
FIG. 3 is a graph demonstrating the hypocholesterolemic effects in chicken eggs after administration of feed supplements comprising *Paecilomyces* sp. fermentation products to egg-laying hens.

Production of Low Cholesterol Eggs Using *Paecilomyces* sp. Culture as Hypocholesterolemic Feed Supplements A culture of *Paecilomyces* sp. (ATCC Accession No. 20463) was prepared and added to commercial chicken feed and the cholesterol content in eggs produced by these chickens was analyzed as described in Example 2. The effect of cholesterol-lowering feed supplements is shown in Table 4 and FIG. 3.

TABLE 4

Cholesterol content of the eggs produced by administration of *Paecilomyces* sp. culture as hypocholesterolemic feed supplements

| Feed supplement | Cholesterol content (mg)/yolk (g) | Cholesterol reduction (%) |
|---|---|---|
| 0% | 16.74 | 0 |
| 1% | 13.31 | 20.5 |
| 5% | 12.67 | 24.4 |

These results demonstrate that the supplemented animal feed of the invention is capable of reducing cholesterol content of egg yolks laid by hens feed the supplemented diet.

EXAMPLE 4

Figure 4:
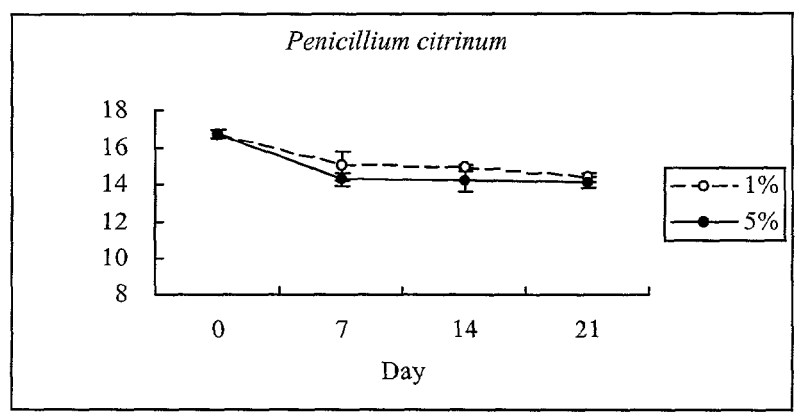
FIG. 4 is a graph demonstrating the hypocholesterolemic effects in chicken eggs after administration of feed supplements comprising *Penicillium citrinum* fermentation products to egg-laying hens.

Production of Low Cholesterol Eggs Using *Penicillium citrinum* Culture as Hypocholesterolemic Feed Supplements A culture of *P. citrinum* (ATCC Accession No. 20606) was prepared and added to commercial chicken feed and the cholesterol content in eggs produced by these chickens was analyzed as described in Example 2. The effect of cholesterol-lowering feed supplements is shown in Table 5 and FIG. 4.

TABLE 5

Cholesterol content of the eggs produced by administration of *P. citrinum* culture as hypocholesterolemic feed supplements

| Feed supplement | Cholesterol content (mg)/yolk (g) | Cholesterol reduction (%) |
|---|---|---|
| 0% | 16.74 | 0 |
| 1% | 14.42 | 13.9 |
| 5% | 14.15 | 15.5 |

These results demonstrate that the supplemented animal feed of the invention is capable of reducing cholesterol content of egg yolks laid by hens feed the supplemented diet.

EXAMPLE 5

Figure 5:
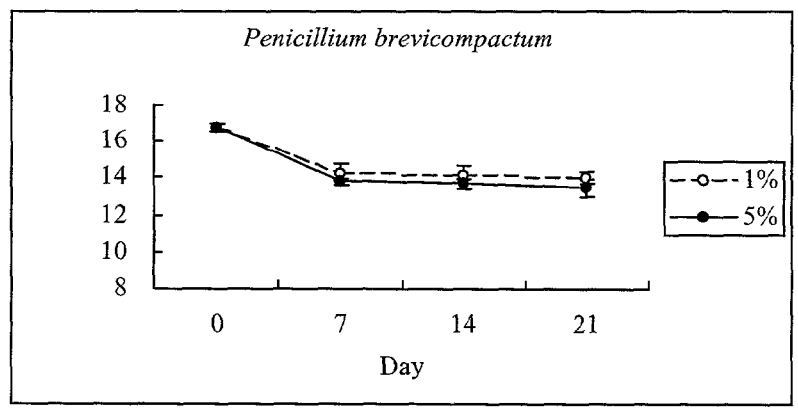
FIG. 5 is a graph demonstrating the hypocholesterolemic effects in chicken eggs after administration of feed supplements comprising *Penicillium brevicompactum* fermentation products to egg-laying hens.

Production of Low Cholesterol Eggs using *Penicillium brevicompactum* Culture as Hypocholesterolemic Feed Supplements A culture of *P. brevicompactum* (ATCC Accession No. 9056) was prepared and added to commercial chicken feed and the cholesterol content in eggs produced by these chickens was analyzed as described in Example 2. The effect of cholesterol-lowering feed supplements is shown in Table 6 and FIG. 5.

TABLE 6

Cholesterol content of the eggs produced by administration of *P. brevicompactum* culture as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.06 | 16 |
| 5% | 13.47 | 19.6 |

These results demonstrate that the supplemented animal feed of the invention is capable of reducing cholesterol content of egg yolks laid by hens feed the supplemented diet.

EXAMPLE 6

Figure 6:
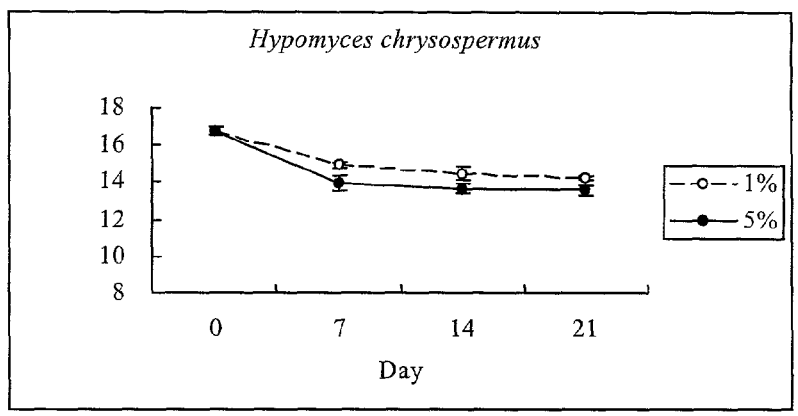
FIG. 6 is a graph demonstrating the hypocholesterolemic effects in chicken eggs after administration of feed supplements comprising *Hypomyces chrysospermus* fermentation products to egg-laying hens.

Production of Low Cholesterol Eggs Using *Hypomyces chrysospermus* Culture as Hypocholesterolemic Feed Supplements A culture of *H. chrysospermus* (IFO Accession No. 7798) was prepared and added to commercial chicken feed and the cholesterol content in eggs produced by these chickens was analyzed as described in Example 2. The effect of cholesterol-lowering feed supplements is shown in Table 7 and FIG. 6.

TABLE 7

Cholesterol content of the eggs produced by administration of *H. chrysospermus* culture as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.26 | 14.8 |
| 5% | 13.58 | 18.9 |

These results demonstrate that the supplemented animal feed of the invention is capable of reducing cholesterol content of egg yolks laid by hens feed the supplemented diet.

EXAMPLE 7

Figure 7:
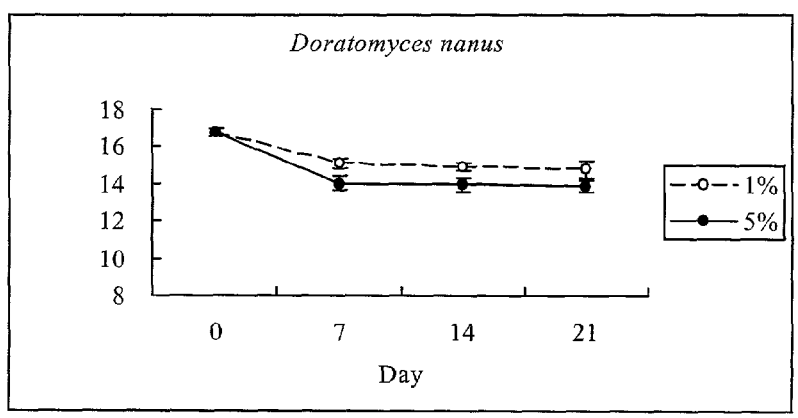
FIG. 7 is a graph demonstrating the hypocholesterolemic effects in chicken eggs after administration of feed supplements comprising *Doratomyces nanus* fermentation products to egg-laying hens.

Production of Low Cholesterol Eggs Using *Doratomyces nanus* Culture as Hypocholesterolemic Feed Supplements A culture of *D. nanus* (IFO Accession No. 9951) was prepared and added to commercial chicken feed and the cholesterol content in eggs produced by these chickens was analyzed as described in Example 2. The effect of cholesterol-lowering feed supplements is shown in Table 8 and FIG. 7.

TABLE 8

Cholesterol content of the eggs produced by administration of *D. nanus* culture as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.79 | 11.6 |
| 5% | 13.87 | 17.1 |

These results demonstrate that the supplemented animal feed of the invention is capable of reducing cholesterol content of egg yolks laid by hens feed the supplemented diet.

EXAMPLE 8

Figure 8:
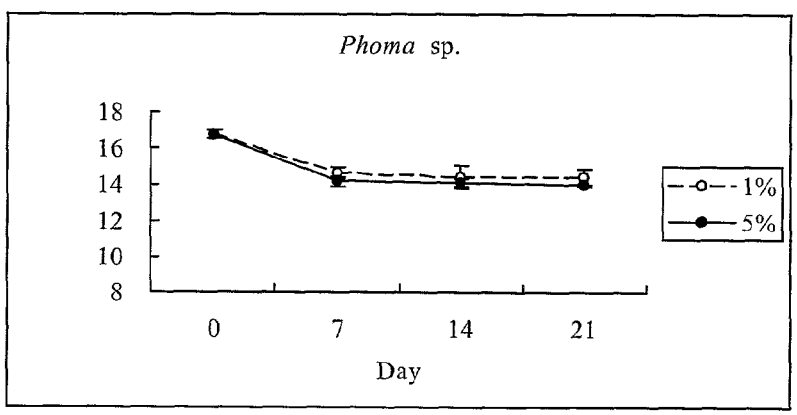
FIG. 8 is a graph demonstrating the hypocholesterolemic effects in chicken eggs after administration of feed supplements comprising *Phoma* sp. fermentation products to egg-laying hens.

Production of Low Cholesterol Eggs Using *Phoma* sp. Culture as Hypocholesterolemic Feed Supplements A culture of *Phoma* sp. (ATCC Accession No. 34505) was prepared and added to commercial chicken feed and the cholesterol content in eggs produced by these chickens was analyzed as described in Example 2. The effect of cholesterol-lowering feed supplements is shown in Table 9 and FIG. 8.

TABLE 9

Cholesterol content of the eggs produced by administration of *Phoma* sp. culture as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.41 | 13.9 |
| 5% | 13.96 | 16.6 |

These results demonstrate that the supplemented animal feed of the invention is capable of reducing cholesterol content of egg yolks laid by hens feed the supplemented diet.

EXAMPLE 9

Figure 9:
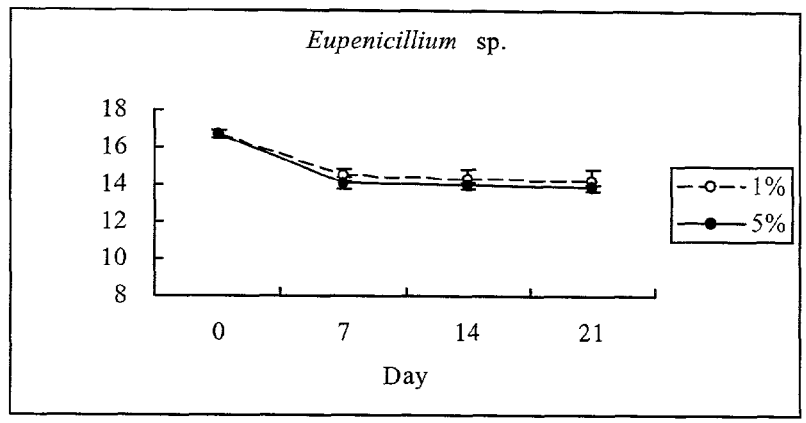
FIG. 9 is a graph demonstrating the hypocholesterolemic effects in chicken eggs after administration of feed supplements comprising *Eupenicillium* sp. fermentation products to egg-laying hens.

Production of Low Cholesterol Eggs Using *Eupenicillium* sp. Culture as Hypocholesterolemic Feed Supplements A culture of *Eupenicillium* sp. (ATCC Accession No. 52642) was prepared and added to commercial chicken feed and the cholesterol content in eggs produced by these chickens was analyzed as described in Example 2. The effect of cholesterol-lowering feed supplements is shown in Table 10 and FIG. 9.

TABLE 10

Cholesterol content of the eggs produced by
administration of *Eupenicillium* sp. culture
as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.25 | 14.9 |
| 5% | 13.85 | 17.3 |

These results demonstrate that the supplemented animal feed of the invention is capable of reducing cholesterol content of egg yolks laid by hens feed the supplemented diet.

EXAMPLE 10

Figure 10:
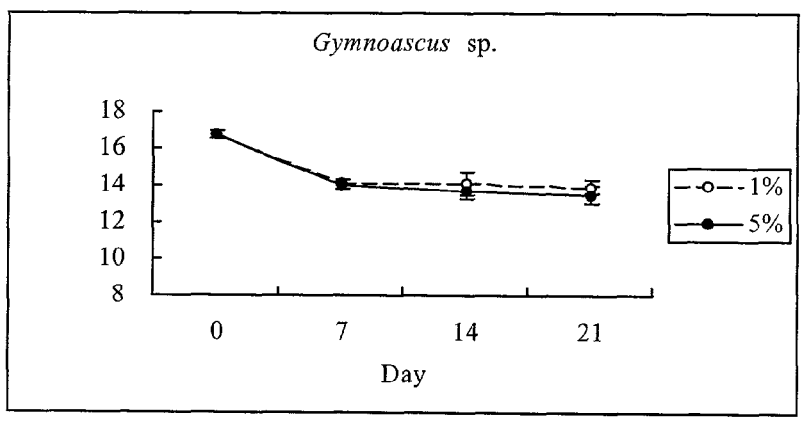
FIG. 10 is a graph demonstrating the hypocholesterolemic effects in chicken eggs after administration of feed supplements comprising *Gymnoascus umbrinus* fermentation products to egg-laying hens.

Production of Low Cholesterol Eggs Using *Gymnoascus umbrinus* Culture as Hypocholesterolemic Feed Supplements A culture of *G. umbrinus* (IFO Accession No. 8450) was prepared and added to commercial chicken feed and the cholesterol content in eggs produced by these chickens was analyzed as described in Example 2. The effect of cholesterol-lowering feed supplements is shown in Table 11 and FIG. 10.

TABLE 11

Cholesterol content of the eggs produced by administration of
*G. umbrinus* culture as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 13.92 | 16.8 |
| 5% | 13.5 | 19.4 |

These results demonstrate that the supplemented animal feed of the invention is capable of reducing cholesterol content of egg yolks laid by hens feed the supplemented diet.

EXAMPLE 11

Figure 11:
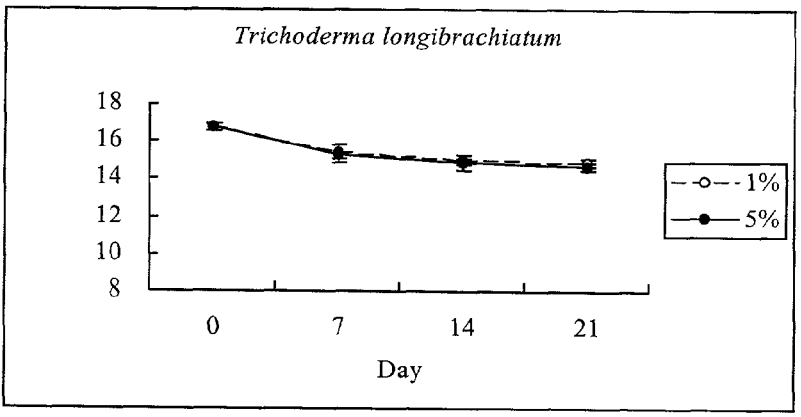

Production of Low Cholesterol Eggs Using *Trichoderma longibrachiatum* Culture as Hypocholesterolemic Feed Supplements A culture of *T. longibrachiatum* (ATCC Accession No. 18648) was prepared and added to commercial chicken feed and the cholesterol content in eggs produced by these chickens was analyzed as described in Example 2. The effect of cholesterol-lowering feed supplements is shown in Table 12 and FIG. 11.

TABLE 12

Cholesterol content of the eggs produced by
administration of *T. longibrachiatum* culture
as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.85 | 11.3 |
| 5% | 14.68 | 12.3 |

These results demonstrate that the supplemented animal feed of the invention is capable of reducing cholesterol content of egg yolks laid by hens feed the supplemented diet.

EXAMPLE 12

Figure 12:
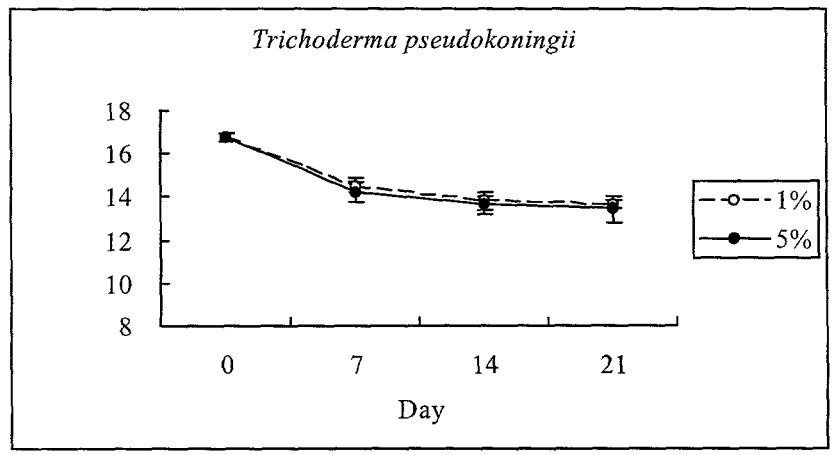
FIG. 12 is a graph demonstrating the hypocholesterolemic effects in chicken eggs after administration of feed supplements comprising *Trichoderma pseudokoningii* fermentation products to egg-laying hens.

Production of Low Cholesterol Eggs Using *Trichoderma pseudokoningii* Culture as Hypocholesterolemic Feed Supplements A culture of *T. pseudokoningii* (ATCC Accession No. 26801) was prepared and added to commercial chicken feed and the cholesterol content in eggs produced by these chickens was analyzed as described in Example 2. The effect of cholesterol-lowering feed supplements is shown in Table 13 and FIG. 12.

TABLE 13

Cholesterol content of the eggs produced by
administration of *T. pseudokoningii* culture
as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 13.67 | 18.4 |
| 5% | 13.43 | 19.8 |

These results demonstrate that the supplemented animal feed of the invention is capable of reducing cholesterol content of egg yolks laid by hens feed the supplemented diet.

EXAMPLE 13

Figure 13:
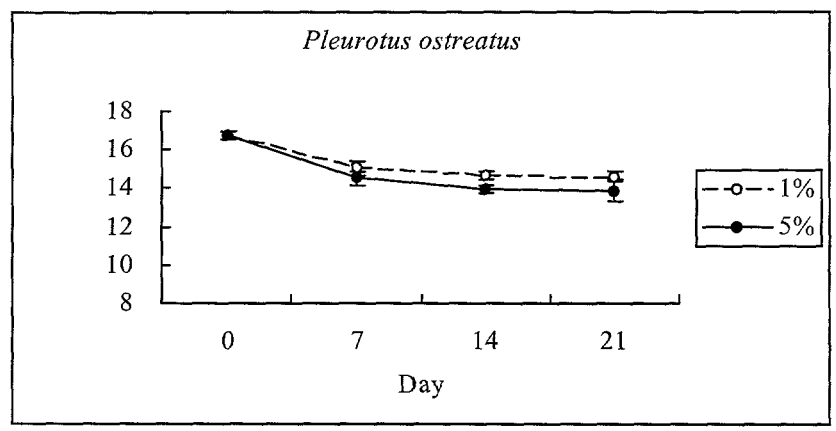
FIG. 13 is a graph demonstrating the hypocholesterolemic effects in chicken eggs after administration of feed supplements comprising *Pleurotus ostreatus* fermentation products to egg-laying hens.

Production of Low Cholesterol Eggs Using *Pleurotus ostreatus* Culture as Hypocholesterolemic Feed Supplements A culture of *P. ostreatus* (ATCC Accession No. 9415) was prepared and added to commercial chicken feed and the cholesterol content in eggs produced by these chickens was analyzed as described in Example 2. The effect of cholesterol-lowering feed supplements is shown in Table 14 and FIG. 13.

TABLE 14

Cholesterol content of the eggs produced by administration of
*P. ostreatus* culture as hypocholesterolemic feed supplements

| Feed supplement | Cholesterol content (mg)/yolk (g) | Cholesterol reduction (%) |
| --- | --- | --- |
| 0% | 16.74 | 0 |
| 1% | 14.59 | 12.8 |
| 5% | 13.87 | 17.1 |

These results demonstrate that the supplemented animal feed of the invention is capable of reducing cholesterol content of egg yolks laid by hens feed the supplemented diet.

EXAMPLE 14

Figure 14:
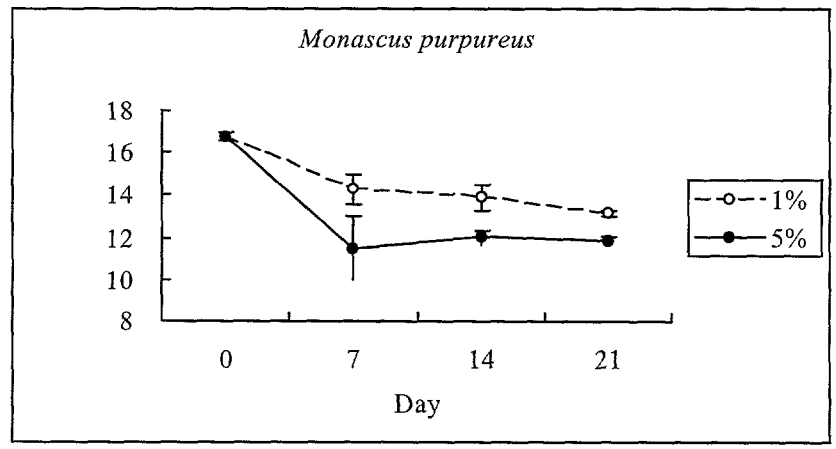
FIG. 14 is a graph demonstrating the hypocholesterolemic effects in chicken eggs after administration of feed supplements comprising *Monascus purpureus* fermentation products to egg-laying hens.

Production of Low Cholesterol Eggs Using *Monascus purpureus* Culture as Hypocholesterolemic Feed Supplements A culture of *M. purpureus* (IFO Accession No. 4513) was prepared and added to commercial chicken feed and the cholesterol content in eggs produced by these chickens was analyzed as described in Example 2. The effect of cholesterol-lowering feed supplements is shown in Table 15 and FIG. 14.

TABLE 15

Cholesterol content of the eggs produced by
administration of *Monascus purpureus* culture
as hypocholesterolemic feed supplements

| Feed supplement | Cholesterol content (mg)/yolk (g) | Cholesterol reduction (%) |
|---|---|---|
| 0% | 16.74 | 0 |
| 1% | 13.16 | 21.4 |
| 5% | 11.87 | 29.1 |

These results demonstrate that the supplemented animal feed of the invention is capable of reducing cholesterol content of egg yolks laid by hens feed the supplemented diet.

EXAMPLE 15

Figure 15:
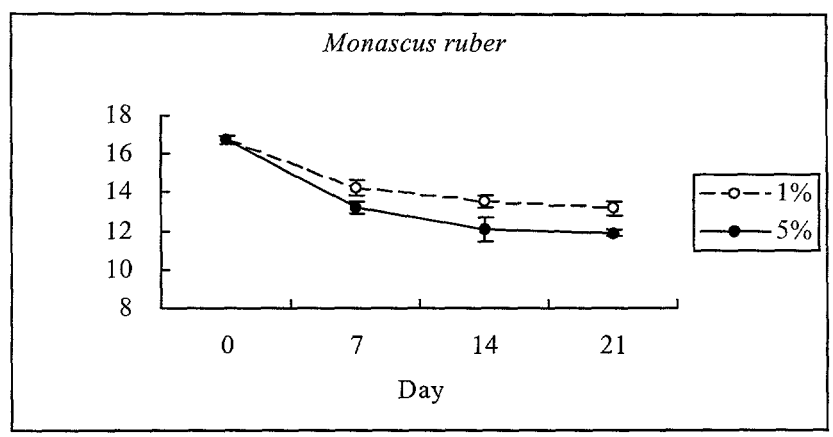
FIG. 15 is a graph demonstrating the hypocholesterolemic effects in chicken eggs after administration of feed supplements comprising *Monascus ruber* fermentation products to egg-laying hens.

Production of Low Cholesterol Eggs Using
*Monascus ruber* Culture as Hypocholesterolemic
Feed Supplements A culture of *M. ruber* (ATCC Accession No. 20657) was prepared and added to commercial chicken feed and the cholesterol content in eggs produced by these chickens was analyzed as described in Example 2. The effect of cholesterol-lowering feed supplements is shown in Table 16 and FIG. 15.

TABLE 16

Cholesterol content of the eggs produced by
administration of *Monascus ruber* culture
as hypocholesterolemic feed supplements

| Feed supplement | Cholesterol content (mg)/yolk (g) | Cholesterol reduction (%) |
|---|---|---|
| 0% | 16.74 | 0 |
| 1% | 13.16 | 21.4 |
| 5% | 11.9 | 28.1 |

These results demonstrate that the supplemented animal feed of the invention is capable of reducing cholesterol content of egg yolks laid by hens feed the supplemented diet.

EXAMPLE 16

Production of Low Cholesterol Poultry Meat Using
Hypocholesterolemic Feed Supplements A fungal culture as described above was added to commercial chicken feed at between 1-5% (by weight) and fed to young chicks (6-9 weeks old) using a schedule of feeding every 12 hours for 3 weeks. Chicken blood was collected and serum was prepared by centrifugation. Sera were analyzed for cholesterol content using the o-phthalaldehyde method described above. Typically, 0.1 mL of sera, 0.3 mL of a 33% (w/v) solution of KOH in water, and 3 mL of 95% ethanol were mixed thoroughly and saponified for 15 min by heating in a heat block at 60°. After saponification, 10 mL of hexane was added and mixed thoroughly. Two mL of freshly prepared o-phthalaldehyde solution (50 mg/dl in glacial acetic acid) was added to 1 mL of extracted cholesterol and incubated for 10 min. Concentrated sulfuric acid (1 mL) was added and incubated for 30 min at room temperature and cholesterol concentration was determined spectrophotometrically by measuring the absorbance 550 nm. Results demonstrating the cholesterol-lowering effect of feed supplements is shown in Table 17.

TABLE 17

Blood cholesterol content of the low cholesterol
chicken produced by administration of microbial culture
as hypocholesterolemic feed supplements.

| Strains | Feed supplement (%) | Cholesterol content (mg)/sera (dl) | Cholesterol reduction (%) |
|---|---|---|---|
| *Aspergillus* | 0% | 144.8 | 0 |
| *Terreus* | 1% | 117.4 | 19 |
|  | 5% | 94.5 | 35 |
| *Paecilomyces* | 0% | 144.8 | 0 |
| sp. | 1% | 124.4 | 14.1 |
|  | 5% | 104.5 | 27.9 |
| *Penicillium* | 0% | 144.8 | 0 |
| *citrinum* | 1% | 122.8 | 15.2 |
|  | 5% | 103.2 | 28.8 |
| *Penicillium* | 0% | 144.8 | 0 |
| *brevicompactum* | 1% | 121.9 | 15.8 |
|  | 5% | 110.3 | 23.8 |
| *Hypomyces* | 0% | 144.8 | 0 |
| *chrysospermus* | 1% | 129.6 | 10.5 |
|  | 5% | 123.2 | 15 |
| *Doratomyces* | 0% | 144.8 | 0 |
| *nanus* | 1% | 128.2 | 11.5 |
|  | 5% | 119.3 | 17.7 |
| *Phoma* sp. | 0% | 144.8 | 0 |
|  | 1% | 131.6 | 9.2 |
|  | 5% | 123.9 | 14.5 |
| *Eupenicillium* | 0% | 144.8 | 0 |
| sp. | 1% | 125.1 | 13.7 |
|  | 5% | 117.8 | 18.7 |
| *Gymnoascus* | 0% | 144.8 | 0 |
| *umbrinus* | 1% | 135.1 | 6.6 |
|  | 5% | 127.1 | 12.3 |
| *Trichoderma* | 0% | 144.8 | 0 |
| *longibrachiatum* | 1% | 131.4 | 9.3 |
|  | 5% | 122.6 | 15.4 |
| *Trichoderma* | 0% | 144.8 | 0 |
| *pseudokoningii* | 1% | 129.3 | 10.8 |
|  | 5% | 121.6 | 16.1 |
| *Pleurotus* | 0% | 144.8 | 0 |
| *ostreatus* | 1% | 134.2 | 7.4 |
|  | 5% | 128.5 | 11.3 |
| *Monascus* | 0% | 144.8 | 0 |
| *purpureus* | 1% | 121.4 | 16.2 |
|  | 5% | 101.5 | 30 |
| *Monascus ruber* | 0% | 144.8 | 0 |
|  | 1% | 120.8 | 16.6 |
|  | 5% | 103.7 | 28.4 |

These results confirmed the cholesterol-lowering effect of hypocholesterolemic feed supplements using microbial cultures containing microorganisms belonging to the genera of *Aspergillus, Paecilomyces, Penicillium, Hypomyces, Doratomyces, Phoma, Eupenicillium, Gymnoascus, Trichoderma, Pleurotus,* and *Monascus*. These results further demonstrated that cultures of *Aspergillus* and *Monascus* were particularly effective in reducing blood cholesterol levels in chickens by up to 30%.

Using chickens fed feed supplemented with microbial cultures of *Aspergillus* or *Monascus* sp., the cholesterol content of breast and leg muscle were analyzed. For this analysis, chickens were bled by heart puncture with syringes and killed by asphyxiation. Breast and leg muscle samples were thoroughly homogenized and 10 g of samples were extracted by the method of Folch et al. (1957, *J. Biol. Chem.* 226: 497) as modified by Bligh and Dryer (1959, *Can. J. Biochem. Physiol.* 37: 911). Briefly, a mixture of chloroform/methanol (10 mL, 2:1 v/v) was added to 1 g of each muscle sample and homogenized. The homogeneous solution was filtered through a glass microfiber filter and the filtrates were diluted to final volume of 20 mL with chloroform/methanol (2:1 v/v). The total cholesterol content was then determined using the o-phthalaldehyde method as described above. Typically, a 2 mL-aliquot (equivalent to 0.1 g tissue) was freed of solvent using a stream of nitrogen while the tube containing the extract was warmed in a 55-60° C. water bath and saponified with 0.3 mL of a solution of 33% (w/v) KOH in water and 3 mL of 95% ethanol for 15 min with heating at 60° C. using a heat block. After saponification, 10 mL of n-hexane was added and mixed thoroughly. Two mL of freshly prepared o-phthalaldehyde solution (50 mg/dl in glacial acetic acid) was added to 1 mL of extracted cholesterol and incubated for 10 min. Concentrated sulfuric acid (1 mL) was added and incubated for 30 min at room temperature and cholesterol concentration was determined spectrophotometrically by measuring the absorbance 550 nm. Results demonstrating the cholesterol-lowering effect of feed supplements in poultry meat is shown in Table 18.

TABLE 18

Cholesterol reduction in chicken meats produced by supplementation of 5% microbial culture to the general feed.

| Feed added with 5% culture | Brest muscle cholesterol content (mg/100 g) | Breast muscle cholesterol reduction (%) | Leg cholesterol content (mg/100 g) | Leg cholesterol reduction (%) |
| --- | --- | --- | --- | --- |
| General feed only | 68 | 0 | 88 | 0 |
| A. terreus | 47 | 31 | 63 | 28 |
| M. purpureus | 44 | 35 | 53 | 38 |
| M. ruber | 46 | 32 | 54 | 38 |

These results confirmed the cholesterol-lowering effect of hypocholesterolemic feed supplements using microbial cultures containing microorganisms belonging to the genera of *Aspergillus* and *Monascus*. Feed supplemented with 5% microbial cultures reduced cholesterol content of chicken breast muscle up to 35% (*M. purpureus*) and of leg close to 40% (*M. purpureus* and *M. ruber*).

EXAMPLE 17

Production of Low Cholesterol Pork Meat Using Hypocholesterolemic Feed Supplements Conventional pig feed was supplemented with between 1 and 5% (by weight) of a fungal culture according to the invention and fed to young pigs (4 months old) in every 12 hours for 2 weeks. Pig sera were analyzed for cholesterol content using the o-phthalaldehyde method described in Example 16. The cholesterol-lowering effect of feed supplements is shown in Table 19.

TABLE 19

Cholesterol content of the pig sera produced by administration of microbial culture as feed supplements.

| strains | Added microbial culture (%) | Cholesterol content (mg)/sera (dl) | Cholesterol reduction (%) |
| --- | --- | --- | --- |
| Aspergillus terreus | 0% | 126.5 | 0 |
| | 1% | 100.7 | 20.4 |
| | 5% | 82.1 | 35.1 |

TABLE 19-continued

Cholesterol content of the pig sera produced by administration of microbial culture as feed supplements.

| strains | Added microbial culture (%) | Cholesterol content (mg)/sera (dl) | Cholesterol reduction (%) |
| --- | --- | --- | --- |
| Paecilomyces sp. | 0% | 126.5 | 0 |
| | 1% | 106.3 | 16 |
| | 5% | 98.6 | 22.1 |
| Penicillium citrinum | 0% | 126.5 | 0 |
| | 1% | 100.7 | 20.4 |
| | 5% | 93.9 | 25.8 |
| Penicillium brevicompactum | 0% | 126.5 | 0 |
| | 1% | 106.3 | 16 |
| | 5% | 97.4 | 23.1 |
| Hypomyces chrysospermus | 0% | 126.5 | 0 |
| | 1% | 110.6 | 12.6 |
| | 5% | 102.4 | 19.1 |
| Doratomyces nanus | 0% | 126.5 | 0 |
| | 1% | 113.7 | 10.2 |
| | 5% | 99.5 | 21.4 |
| Phoma sp. | 0% | 126.5 | 0 |
| | 1% | 107.8 | 14.8 |
| | 5% | 97.5 | 23 |
| Eupenicillium sp. | 0% | 126.5 | 0 |
| | 1% | 109.6 | 13.4 |
| | 5% | 101.4 | 20 |
| Gymnoascus umbrinus | 0% | 126.5 | 0 |
| | 1% | 111.2 | 12.1 |
| | 5% | 102.8 | 18.8 |
| Trichoderma longibrachiatum | 0% | 126.5 | 0 |
| | 1% | 109.9 | 13.2 |
| | 5% | 103.7 | 18.1 |
| Trichoderma pseudokoningii | 0% | 126.5 | 0 |
| | 1% | 106.4 | 15.9 |
| | 5% | 101.5 | 19.8 |
| Pleurotus ostreatus | 0% | 126.5 | 0 |
| | 1% | 107.3 | 15.2 |
| | 5% | 98.9 | 21.9 |
| Monascus purpureus | 0% | 126.5 | 0 |
| | 1% | 107.5 | 15.1 |
| | 5% | 91.6 | 27.6 |
| Monascus ruber | 0% | 126.5 | 0 |
| | 1% | 110.5 | 12.7 |
| | 5% | 94.6 | 25.3 |

These results confirmed the cholesterol-lowering effect of hypocholesterolemic feed supplements using microbial cultures containing microorganisms belonging to the genera of *Aspergillus* and *Monascus*. Feed supplemented with 5% microbial cultures reduced cholesterol content of pig sera from 25% (*M. purpureus* and *M. ruber*) to 35% (*A. terreus*).

EXAMPLE 18

Production of Low Cholesterol Beef Meat Using Hypocholesterolemic Feed Supplements Conventional cow feed was supplemented with between 1 and 5% (by weight) of a fungal culture according to the invention and fed to young cows (2 years old) in every 12 hours for 3 weeks. Cow sera were analyzed for cholesterol content using the o-phthalaldehyde method described in Example 16. The cholesterol-lowering effect of feed supplements is shown in Table 20.

TABLE 20

Cholesterol content of the cow sera after administration of microbial culture as feed supplements.

| strains | Added microbial culture (%) | Cholesterol content (mg)/sera (dl) | Cholesterol reduction (%) |
|---|---|---|---|
| Aspergillus terreus | 0% | 192.8 | 0 |
| | 1% | 178.5 | 7.5 |
| | 5% | 169.3 | 12.2 |
| Paecilomyces sp. | 0% | 192.8 | 0 |
| | 1% | 182.5 | 5.4 |
| | 5% | 179.8 | 6.8 |
| Penicillium citrinum | 0% | 192.8 | 0 |
| | 1% | 181.3 | 6 |
| | 5% | 176.6 | 8.5 |
| Penicillium brevicompactum | 0% | 192.8 | 0 |
| | 1% | 180.7 | 6.3 |
| | 5% | 174.3 | 9.6 |
| Hypomyces chrysospermus | 0% | 192.8 | 0 |
| | 1% | 184.3 | 4.5 |
| | 5% | 181.4 | 6 |
| Doratomyces nanus | 0% | 192.8 | 0 |
| | 1% | 185.2 | 4 |
| | 5% | 181.3 | 6 |
| Phoma sp. | 0% | 192.8 | 0 |
| | 1% | 184.7 | 4.3 |
| | 5% | 179.7 | 6.8 |
| Eupenicillium sp. | 0% | 192.8 | 0 |
| | 1% | 185.3 | 3.9 |
| | 5% | 182.9 | 5.2 |
| Gymnoascus umbrinus | 0% | 192.8 | 0 |
| | 1% | 182.5 | 5.4 |
| | 5% | 178.6 | 7.4 |
| Trichoderma longibrachiatum | 0% | 192.8 | 0 |
| | 1% | 181.5 | 5.9 |
| | 5% | 175.4 | 9.1 |
| Trichoderma pseudokoningii | 0% | 192.8 | 0 |
| | 1% | 180.8 | 6.3 |
| | 5% | 176.9 | 8.3 |
| Pleurotus ostreatus | 0% | 192.8 | 0 |
| | 1% | 184.6 | 4.3 |
| | 5% | 179.3 | 7.1 |
| Monascus purpureus | 0% | 192.8 | 0 |
| | 1% | 178.4 | 7.5 |
| | 5% | 174.2 | 9.7 |
| Monascus ruber | 0% | 192.8 | 0 |
| | 1% | 175.0 | 9.3 |
| | 5% | 171.3 | 11.2 |

These results confirmed the cholesterol-lowering effect of hypocholesterolemic feed supplements using microbial cultures containing microorganisms belonging to the genera of *Aspergillus* and *Monascus*. Feed supplemented with 5% microbial cultures reduced cholesterol content of cow sera by greater than 10% (*M. ruber* and *A. terreus*).

EXAMPLE 19

Production of Low Cholesterol Milk Using Hypocholesterolemic Feed Supplements

Conventional dairy cow feed was supplemented with between 1 and 5% (by weight) of a fungal culture according to the invention and fed to young milking cows (25 months old) in every 12 hours for 3 weeks. Milk samples were analyzed for cholesterol content using the o-phthalaldehyde method described in Example 16. The cholesterol-lowering effect of feed supplements is shown in Table 21.

TABLE 21

Cholesterol content of the milk after administration of microbial culture as feed supplements.

| Strains | Added microbial culture (%) | Cholesterol content (mg)/milk (dl) | Cholesterol reduction (%) |
|---|---|---|---|
| Aspergillus terreus | 0% | 10.16 | 0 |
| | 1% | 7.26 | 28.5 |
| | 5% | 6.52 | 35.9 |
| Paecilomyces sp. | 0% | 10.16 | 0 |
| | 1% | 8.47 | 16.7 |
| | 5% | 7.82 | 23.1 |
| Penicillium citrinum | 0% | 10.16 | 0 |
| | 1% | 8.39 | 17.5 |
| | 5% | 8.02 | 21.1 |
| Penicillium brevicompactum | 0% | 10.16 | 0 |
| | 1% | 8.48 | 16.5 |
| | 5% | 7.94 | 21.9 |
| Hypomyces chrysospermus | 0% | 10.16 | 0 |
| | 1% | 8.82 | 13.2 |
| | 5% | 8.53 | 16.1 |
| Doratomyces nanus | 0% | 10.16 | 0 |
| | 1% | 8.61 | 15.3 |
| | 5% | 8.29 | 18.5 |
| Phoma sp. | 0% | 10.16 | 0 |
| | 1% | 8.71 | 14.3 |
| | 5% | 8.56 | 15.8 |
| Eupenicillium sp. | 0% | 10.16 | 0 |
| | 1% | 9.02 | 11.3 |
| | 5% | 8.88 | 12.6 |
| Gymnoascus umbrinus | 0% | 10.16 | 0 |
| | 1% | 8.59 | 15.5 |
| | 5% | 8.21 | 19.2 |
| Trichoderma longibrachiatum | 0% | 10.16 | 0 |
| | 1% | 8.59 | 15.5 |
| | 5% | 8.12 | 20.1 |
| Trichoderma pseudokoningii | 0% | 10.16 | 0 |
| | 1% | 8.65 | 14.9 |
| | 5% | 8.48 | 16.6 |
| Pleurotus ostreatus | 0% | 10.16 | 0 |
| | 1% | 8.32 | 18.2 |
| | 5% | 8.08 | 20.5 |
| Monascus purpureus | 0% | 10.16 | 0 |
| | 1% | 8.09 | 20.4 |
| | 5% | 7.87 | 22.6 |
| Monascus ruber | 0% | 10.16 | 0 |
| | 1% | 8.12 | 20.1 |
| | 5% | 7.69 | 24.4 |

These results confirmed the cholesterol-lowering effect of hypocholesterolemic feed supplements using microbial cultures containing microorganisms belonging to the genera of *Aspergillus* and *Monascus*. Feed supplemented with 5% microbial cultures reduced cholesterol content of cow's milk from 20% (*M. ruber* and *M. purpureus*) to almost 40% by greater than 10% (*A. terreus*).

It should be understood that the foregoing disclosure emphasizes certain specific embodiments of the invention and that all modifications or alternatives equivalent thereto are within the spirit and scope of the invention as set forth in the appended claims.

We claim:

1. An animal feed composition, comprising an active microbial culture in fermentation media capable of producing within the animal feed composition hypocholesterolemic compounds effective in reducing blood cholesterol in an animal, wherein the microbial culture is 0.1-30% of the animal feed composition, and wherein the fermentation media comprises either a carbon source, a nitrogen source, or both a carbon and nitrogen source to provide an amino acid-rich fermentation media sufficient to facilitate production of the hypocholesterolemic compounds.

2. An animal feed composition, comprising an active microbial culture in fermentation media capable of producing within the animal feed composition hypocholesterolemic compounds effective in reducing blood cholesterol in an animal, wherein the microbial culture is 0.1-30% of the animal feed composition, wherein the hypocholesterolemic compounds are effective in lowering blood cholesterol concentration of animals by inhibiting the cholesterol biosynthesis, by inhibiting re-absorption of bile acids along digestive tracts, and/or by facilitating conversion of cholesterols to bile acids, and wherein the fermentation media comprises either a carbon source, a nitrogen source, or both a carbon and nitrogen source to provide an amino acid-rich fermentation media sufficient to facilitate production of the hypocholesterolemic compounds.

3. The animal feed composition of claim 1, wherein the hypocholesterolemic compounds is monacolin K (mevinolin), monacolin L, monacolin J, monacolin X, monacolin M, lovastatin, compactin or mixtures thereof.

4. The animal feed composition of claim 1, wherein the active microbial culture is a single or mixed culture comprising microorganisms of genera *Aspergillus, Paecilomyces, Penicillium, Hypomyces, Doratomyces, Phoma, Eupenicillium, Gymnoascus, Trichoderma, Pleurotus, Monascus, Coniothyrium, Eubacterium* or *Nocardia*.

5. The animal feed composition of claim 1, wherein the fermentation media comprises cotton seed extracts, a powder or mixture of sugar, rice, corn, potato, or wheat, and sodium (Na), calcium (Ca), iron (Fe), copper (Cu), and manganese (Mn) as trace elements.

6. The animal feed composition of claim 1 or 5, wherein the fermentation media comprises 0.5-1.5% cotton seed extracts, 1.5-4% of a carbon source, 0.1-0.5% NaCl, 0.1-0.5% $CaCO_3$, 0.01-0.04% $FeCl_3.6H_2O$, 0.001-0.002% $CuCl_2.2H_2O$, 0.001-0.002% $MnCl_2.4H_2O$, 0.002-0.006% $ZnCl_2$, 0.001-0.002% $Na_2B_4O_7.10H_2O$, and 0.001-0.002% $(NH_4)6Mo_7O_{24}.4H_2O$ in water.

* * * * *